United States Patent
Hashimoto et al.

(10) Patent No.: US 11,672,462 B2
(45) Date of Patent: Jun. 13, 2023

(54) MEASUREMENT CONTROL APPARATUS AND MEASUREMENT CONTROL METHOD

(71) Applicant: Nippon Telegraph and Telephone Corporation, Tokyo (JP)

(72) Inventors: Yuki Hashimoto, Tokyo (JP); Kei Kuwabara, Tokyo (JP); Nobuaki Matsuura, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 161 days.

(21) Appl. No.: 17/434,128

(22) PCT Filed: Feb. 21, 2020

(86) PCT No.: PCT/JP2020/007059
§ 371 (c)(1),
(2) Date: Aug. 26, 2021

(87) PCT Pub. No.: WO2020/179499
PCT Pub. Date: Sep. 10, 2020

(65) Prior Publication Data
US 2022/0142550 A1 May 12, 2022

(30) Foreign Application Priority Data
Mar. 7, 2019 (JP) .............................. JP2019-041198

(51) Int. Cl.
*A61B 5/352* (2021.01)
*A61B 5/0245* (2006.01)
*A61B 5/00* (2006.01)

(52) U.S. Cl.
CPC ............ *A61B 5/352* (2021.01); *A61B 5/0245* (2013.01); *A61B 5/7225* (2013.01); *A61B 2560/0209* (2013.01); *A61B 2560/0214* (2013.01)

(58) Field of Classification Search
None
See application file for complete search history.

(56) References Cited

U.S. PATENT DOCUMENTS 5,935,069 A * 8/1999 Chandler ............... A61B 8/543
600/458
2006/0173369 A1 8/2006 Kaski
(Continued)

FOREIGN PATENT DOCUMENTS

JP 2014135987 A 7/2014
JP 2015156936 A 9/2015
(Continued)

OTHER PUBLICATIONS

Ministry of Internal Affairs and Communications, White Paper on Information and Communications, 2018, 3 pages.

*Primary Examiner* — Ankit D Tejani
(74) *Attorney, Agent, or Firm* — Slater Matsil, LLP

(57) ABSTRACT

A measurement control apparatus includes a sensor data acquisition unit configured to acquire biological information of a user measured by a sensor, an extraction unit configured to extract a feature quantity with periodicity from the biological information acquired by the sensor data acquisition unit, an interval acquisition unit configured to acquire a period of the extracted feature quantity, a determination unit configured to determine whether or not the feature quantity will have appeared by a set end time on the basis of the acquired period of the feature quantity, and a termination processing unit configured to terminate an operation of the sensor data acquisition unit when the determination unit determines that the feature quantity will not have appeared by the set end time.

13 Claims, 5 Drawing Sheets

(56) References Cited

U.S. PATENT DOCUMENTS

2006/0224190 A1* 10/2006 Gill .................. A61N 1/36564
607/3
2017/0224244 A1    8/2017 Kuwabara et al.
2019/0069791 A1    3/2019 Matsuura et al.

FOREIGN PATENT DOCUMENTS

| JP | 2018011819 A  | 1/2018 |
| WO | 2016024495 A1 | 2/2016 |
| WO | 2017150156 A1 | 9/2017 |

* cited by examiner

MEASUREMENT CONTROL APPARATUS AND MEASUREMENT CONTROL METHOD

CROSS-REFERENCE TO RELATED APPLICATIONS

This application is a national phase entry of PCT Application No. PCT/JP2020/007059, filed on Feb. 21, 2020, which claims priority to Japanese Application No. 2019-041198, filed on Mar. 7, 2019, which applications are hereby incorporated herein by reference.

TECHNICAL FIELD

The present invention relates to a measurement control apparatus and a measurement control method, and particularly, to a technology for controlling a measurement operation of biological information.

BACKGROUND

In recent years, wearable devices have been attracting attention as representative communication terminals in an IoT era. An example of the wearable devices includes a consumer device such as smart watch, or a healthcare terminal that is attached to clothing to monitor biological information such as the number of steps, an activity amount, or a heart rate of a user. Further, wearable devices for business use that monitor work or an environment of employees have also been developed, and some wearable devices have already been put into practical use (see NPL 1).

In particular, for wearable devices for healthcare use, growing health consciousness according to global aging or a demand for point of care has also been attracting attention. The wearable devices for healthcare are able to review or improve lifestyle habits and prevent diseases such as lifestyle-related diseases by utilizing monitoring information through measurement or monitoring of biological information in daily life. Therefore, the wearable devices for healthcare are expected to maintain and improve people's living standards.

As an example, PTL 1 discloses an application in which a user wears clothing to which a sensor terminal is attached so that a biological state such as a stress state of a user estimated from an electrocardiographic waveform of the user, a heart rate of the user, and an R wave interval is acquired.

Generally, in such a wearable device of the related art, a battery occupies a large proportion of a mass and a volume of the entire device. It is necessary to reduce a battery capacity in order to reduce a weight and size of the device. Therefore, power saving of the entire device is required. Further, in the case of a device in which monitoring for a long time in daily life such as heart rate measurement is assumed, reduction of power consumption at the time of an operation of the device can be said to be an important technical issue.

In response to such a problem, a heart rate measurement apparatus described in PTL 1 intermittently executes transmission of data to an external device while temporarily accumulating measurement data so that power saving is achieved. However, measurement of the electrocardiographic signal itself is always executed, and it can be said that there is still room for decreasing power consumption of an intermittent operation of heart rate measurement itself, or the like.

CITATION LIST

Patent Literature

PTL 1—WO 2016/024495
PTL 2—Japanese Patent Application Publication No. 2018-011819
PTL 3 Republished International Patent Publication No. WO 2017/150156
PTL 4 Japanese Patent Application Publication No. 2015-156936

Non Patent Literature

NPL 1—"2018 White Paper on Information and Communications" Ministry of Internal Affairs and Communications: pp. 14-15

SUMMARY

Technical Problem

Embodiments of the present invention have been made to solve the above-described problems, and an object of embodiments of the present invention is to provide a measurement control technology capable of performing measurement of biological information with more power saving.

Means for Solving the Problem

In order to solve the above-described problem, a measurement control apparatus according to embodiments of the present invention includes a sensor data acquisition unit configured to acquire biological information of a user measured by a sensor; an extraction unit configured to extract a feature quantity with periodicity from the biological information acquired by the sensor data acquisition unit; an interval acquisition unit configured to acquire a period of the extracted feature quantity; a determination unit configured to determine whether or not the feature quantity will have appeared by a set end time on the basis of the acquired period of the feature quantity; and a termination processing unit configured to terminate an operation of the sensor data acquisition unit when the determination unit determines that the feature quantity will not have appeared by the set end time.

Further, in the measurement control apparatus according to embodiments of the present invention, the termination processing unit may stop the acquisition of the biological information by the sensor data acquisition unit.

Further, in the measurement control apparatus according to embodiments of the present invention, the termination processing unit may stop supply of power to the sensor data acquisition unit.

Further, in the measurement control apparatus according to embodiments of the present invention, the sensor data acquisition unit may amplify an analog signal indicating the biological information, and discretize the amplified analog signal in a preset sampling period to convert the analog signal into a digital signal.

Further, in the measurement control apparatus according to embodiments of the present invention, the sensor data acquisition unit may acquire an electrocardiographic signal of the user from the sensor including an electrocardiograph.

Further, in the measurement control apparatus according to embodiments of the present invention, the extraction unit may extract an R wave included in the electrocardiographic signal as the feature quantity, the interval acquisition unit may acquire an R-R interval indicating an interval of the R wave as the period, and the determination unit may determine whether or not the R wave will have appeared at the set end time on the basis of the R-R interval.

Further, in the measurement control apparatus according to embodiments of the present invention, the determination unit may determine whether or not the R wave will have appeared by the set end time through comparison with the set end time on the basis of any time at which the sensor data acquisition unit acquires the electrocardiographic signal and a predicted time at which the next R wave will appear, the predicted time being estimated on the basis of an instantaneous heart rate or an average heart rate calculated from a latest R-R interval acquired by the interval acquisition unit.

Further, in order to solve the above-described problem, a measurement control method according to embodiments of the present invention includes a first step of acquiring biological information of a user measured by a sensor; a second step of extracting a feature quantity with periodicity from the biological information acquired in the first step; a third step of acquiring the period of the extracted feature quantity; a fourth step of determining whether or not the feature quantity will have appeared by a set end time on the basis of the acquired period of the feature quantity; and a fifth step of terminating the acquisition of the biological information in the first step when it is determined in the fourth step that the feature quantity will not have appeared by the set end time.

Effects of Embodiments of the Invention

According to embodiments of the present invention, since it is determined whether or not the feature quantity will have appeared by the set end time on the basis of the acquired period of the feature quantity of the biological information of the user, and the acquisition of the biological information is ended when the feature quantity will not have appeared, it is possible to perform the measurement of the biological information with more power saving.

DETAILED DESCRIPTION OF ILLUSTRATIVE EMBODIMENTS

Hereinafter, a preferred embodiment of the present invention will be described in detail with reference to FIGS. 1 to 5. Further, an example in which an electrocardiographic signal of a user is used as biological information that is measured by a measurement control apparatus 1, an R wave is extracted as a feature quantity of the electrocardiographic signal, and a heart rate of the user is measured on the basis of the number of R waves of an electrocardiographic waveform per minute will be described in the present embodiment.

The measurement control apparatus 1 according to the present embodiment repeats a normal operation and a standby operation in a preset period of time to perform control of an intermittent operation in which the heart rate of the user is measured. In the normal operation, the heart rate of the user is measured, and in standby operation, the heart rate of the user is not measured.

A sensor 2 includes, for example, an electrocardiograph, and is attached to the user to measure the electrocardiographic signal of the user.

Overview of Measurement Control Apparatus

Figure 1:
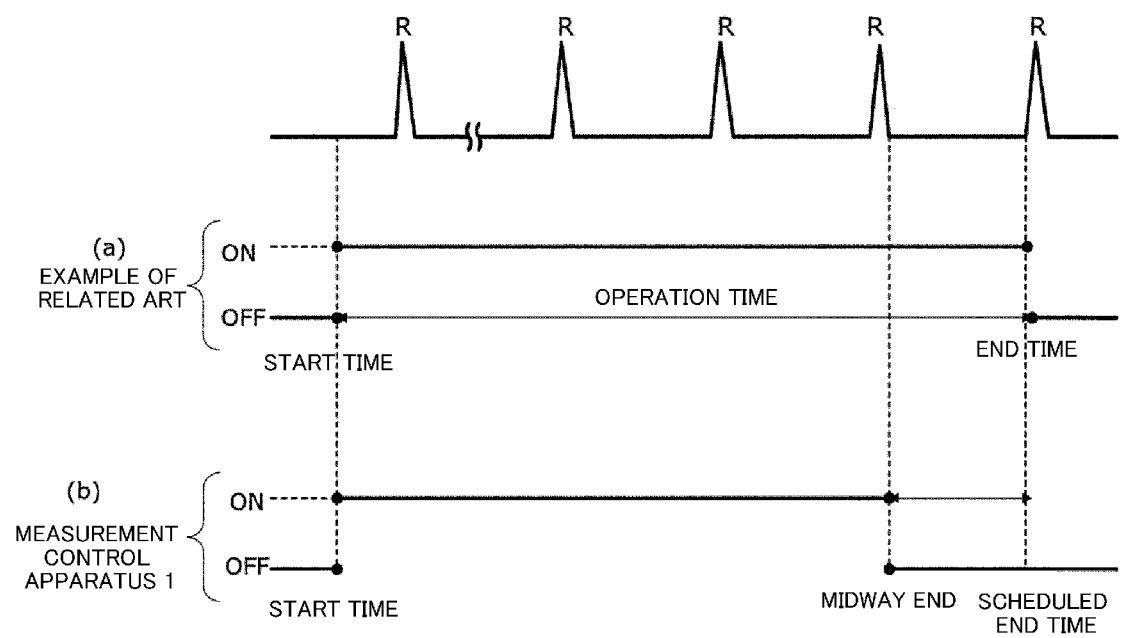
FIG. 1 is a diagram illustrating an overview of a measurement control apparatus according to an embodiment of the present invention.

FIG. 1 is a diagram illustrating an example of control of time-series data and measurement time of R wave extracted from electrocardiographic waveform of a user. FIG. 1(a) illustrates R wave detection control in a measurement control apparatus according to an example of the related art. The measurement control apparatus according to the example of the related art intermittently measures a heart rate of a user on the basis of a predefined time in which an electrocardiographic waveform is acquired and a heart rate is detected (normal operation: ON) and a time in which the measurement control apparatus is put in a standby state (standby operation: OFF). Thus, in the measurement control apparatus according to the example of the related art, the measurement is continued until a set end time of the normal operation.

On the other hand, the measurement control apparatus 1 according to the present embodiment acquires the R-R interval at a timing at which the R wave is detected as illustrated in FIG. 1(b), and determines whether or not the R wave will have appeared by the set end time on the basis of the acquired R-R interval, in addition to the intermittent operation. The measurement control apparatus 1 continues the measurement when the measurement control apparatus 1 determines that the R wave will have appeared by the set end time, but terminates the normal operation of measuring the heart rate at a time point at which the R wave that appears last has been measured, when the measurement control apparatus 1 determines that the R wave will not have appeared by the set end time. When the measurement control apparatus 1 terminates the measurement before the end time is reached as illustrated in FIG. 1(b), it is possible to reduce a useless operation time in a period of time in which no R wave is detected, and it is possible to achieve power saving of a measurement system. The heart rate is calculated using the R-R interval.

Functional Blocks of Measurement Control Apparatus

Figure 2:
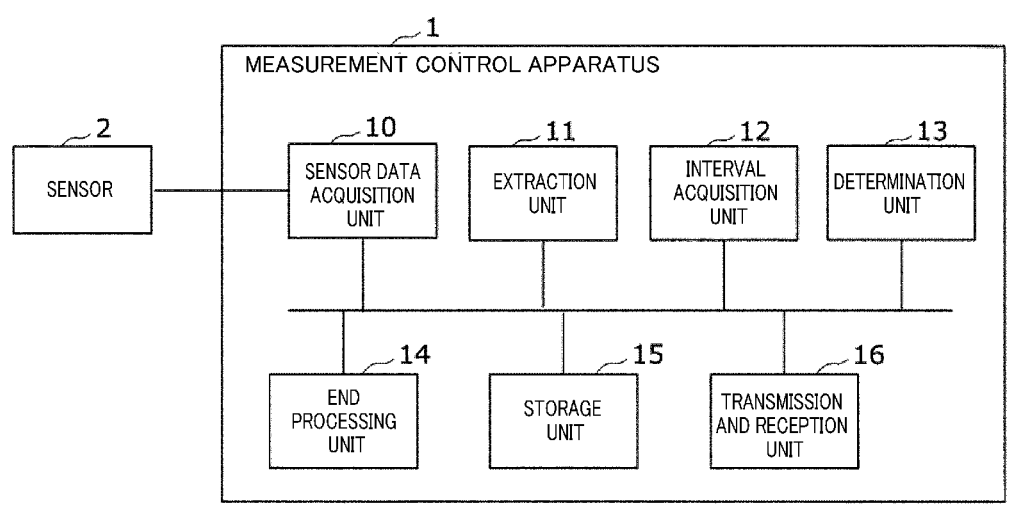
FIG. 2 is a block diagram illustrating a functional configuration of the measurement control apparatus according to the embodiment of the present invention.

Next, a functional configuration of the measurement control apparatus 1 according to the present embodiment will be described with reference to FIG. 2. As illustrated in FIG. 2, the measurement control apparatus 1 includes a sensor data acquisition unit 10, an extraction unit 11, an interval acquisition unit 12, a determination unit 13, a termination processing unit 14, a storage unit 15, and a transmission and reception unit 16.

The sensor data acquisition unit 10 acquires biological information of the user from the sensor 2. More specifically, the sensor data acquisition unit 10, for example, acquires the electrocardiographic signal of the user from the sensor 2 configured of the electrocardiograph in a preset period of time from a start time to a end time of the normal operation. The sensor data acquisition unit 10 amplifies the electrocardiographic signal of the user acquired from the sensor 2, and converts the amplified electrocardiographic signal that is an analog signal into a digital signal at a predetermined sampling frequency. Further, the sensor data acquisition unit 10 removes noise from the acquired electrocardiographic waveform as necessary. The electrocardiographic waveform of the user acquired by the sensor data acquisition unit 10 is stored in the storage unit 15.

The extraction unit 11 extracts a feature quantity having periodicity from time-series data of biological information of the user acquired by the sensor data acquisition unit 10. Specifically, the extraction unit 11 extracts an R wave, which is one of main components, from the electrocardiographic waveform acquired by the sensor data acquisition unit 10.

The interval acquisition unit 12 acquires a period of the feature quantity of the biological information extracted by the extraction unit 11. Specifically, the interval acquisition unit 12 acquires the R-R interval, which is a period of the R wave extracted from the electrocardiographic waveform by the extraction unit 11. The interval acquisition unit 12 may perform calculation using the latest instantaneous heart rate or average heart rate (see PTL 2) when acquiring the R-R interval. The acquired R-R interval is stored in the storage unit 15. In the present embodiment, the R-R interval acquired by the interval acquisition unit 12 is used as the heart rate of the user.

The determination unit 13 determines whether or not the feature quantity will have appeared by the set end time of the normal operation on the basis of the period of the feature quantity acquired by the interval acquisition unit 12. When the determination unit 13 determines that the feature quantity of the biological information will not have appeared by the set end time, the determination unit 13 outputs a termination signal indicating that the normal operation will be terminated before the end time of the normal operation. Specifically, the determination unit 13 determines whether or not the R wave will have appeared in the time-series data of the R wave by the set end time on the basis of the R-R interval, and outputs a termination signal when the R wave will not have appeared.

The termination processing unit 14 terminates an operation of the sensor data acquisition unit 10 when the determination unit 13 determines that the feature quantity will not have appeared by the set end time. More specifically, the termination processing unit 14 stops the acquisition of the biological information by the sensor data acquisition unit 10 when there is an input of a termination signal from the determination unit 13. More specifically, the termination processing unit 14 can stop power supply from a power supply apparatus 11o to be described below to the sensor data acquisition unit 10.

When the termination processing unit 14 stops the acquisition of the biological information by the sensor data acquisition unit 10, a transition from the normal operation for measuring the heart rate of the user to the standby operation or a sleep operation occurs. The termination processing unit 14 can perform termination processing such as a standby state in which power is supplied to a memory or a pause state in which memory content or a computer state is evacuated to a hard disk and power is completely turned off according to a hardware configuration of the measurement control apparatus 1, required power consumption, or the like.

The storage unit 15 stores the time-series data of the biological information of the user acquired by the sensor data acquisition unit 10. Further, the storage unit 15 stores the R wave extracted by the extraction unit 11. Further, the storage unit 15 stores the R-R interval acquired by the interval acquisition unit 12. Further, the storage unit 15 stores the preset end time of the normal operation.

The transmission and reception unit 16 transmits the heart rate of the user calculated on the basis of the R-R interval acquired by the interval acquisition unit 12 to an external server, terminal apparatus, or the like. The transmission and reception unit 16 can transmit, for example, an instantaneous heart rate or an average heart rate to the outside. Further, sensor data can be acquired from the sensor 2 via the transmission and reception unit 16.

Hardware Configuration of Measurement Control Apparatus

Next, a hardware configuration of the measurement control apparatus 1 having the above-described functional configuration will be described with reference to a block diagram of FIG. 3.

Figure 3:
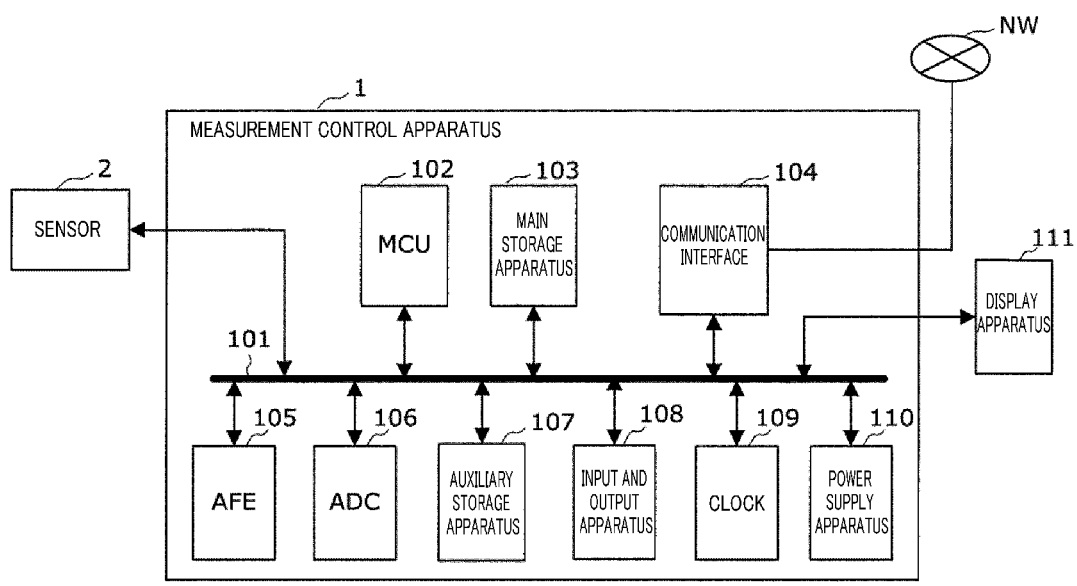
FIG. 3 is a block diagram illustrating a hardware configuration of the measurement control apparatus according to the embodiment of the present invention.

As illustrated in FIG. 3, the measurement control apparatus 1 can be realized by, for example, a computer including a micro control unit (MCU) 102, a main storage apparatus 103, a communication interface 104, an analog front end (AFE) 105, an analog to digital converter (ADC) 106, an auxiliary storage apparatus 107, an input and output apparatus 108, a clock 109, and the power supply apparatus 11o connected via a bus 101, and a program for controlling these hardware resources. In the measurement control apparatus 1, the sensor 2 provided outside and a display apparatus 11 provided inside the measurement control apparatus 1 are connected via the bus 101.

A program for enabling the MCU 102 to perform various controls or calculations is stored in the main storage apparatus 103 in advance. Each function of the measurement control apparatus 1 including the extraction unit 11, the interval acquisition unit 12, the determination unit 13, and the termination processing unit 14 illustrated in FIG. 2 is realized by the MCU 102 and the main storage apparatus 103.

The communication interface 104 is an interface circuit for communicating with various external electronic devices via a communication network NW.

For example, a calculation interface and an antenna corresponding to a wireless data communication standard such as LTE, 3G, wireless LAN, or Bluetooth (registered trademark) Low Energy (BLE) can be used as the communication interface 104. Further, the communication interface 104 can be realized by a communication interface circuit corresponding to a wired communication standard such as Ethernet (registered trademark). The transmission and reception unit 16 described with reference to FIG. 2 is realized by the communication interface 104.

The AFE 105 includes an amplification circuit that amplifies and outputs a weak electrocardiographic signal of the user acquired from the sensor 2.

The ADC 106 includes an analog-to-digital conversion circuit that converts an analog signal amplified by the AFE 105 into a digital signal at a predetermined sampling frequency. The ADC 106 outputs time-series data of the electrocardiographic signal converted into the digital signal. The sensor data acquisition unit 10 described with reference to FIG. 2 is realized by the AFE 105 and the ADC 106.

The auxiliary storage apparatus 107 is configured of a readable and writable storage medium, and a drive apparatus for reading or writing various pieces of information such as programs or data to the storage medium. In the auxiliary storage apparatus 107, a non-volatile memory such as a flash memory can be used as the storage medium. The auxiliary storage apparatus 107 may be realized by, for example, a volatile memory such as a DRAM.

The auxiliary storage apparatus 107 has a storage area in which the biological information measured by the sensor 2 is stored, and a program storage area in which a program enabling the measurement control apparatus 1 to perform control of the measurement of the biological information is stored. The storage unit 15 described with reference to FIG. 2 is realized by the auxiliary storage apparatus 107. Further, for example, the auxiliary storage apparatus 107 may have a backup area for backing up, for example, the data or program described above.

The input and output apparatus 108 is configured of an I/O terminal for inputting a signal from an external device such as the sensor 2 or the display apparatus 111 and outputting a signal to the external device.

The clock 109 is configured of, for example, a built-in clock built in the computer and measures a time. The time information obtained by the clock 109 is referred to when the sensor data is sampled or when the MCU 102 (the extraction unit 11, the interval acquisition unit 12, the determination unit 13, and the termination processing unit 14) uses the time information.

The power supply apparatus 110 is realized by a power supply circuit that supplies power to the entire measurement control apparatus 1 including the MCU 102, the main storage apparatus 103, the communication interface 104, the AFE 105, the ADC 106, the auxiliary storage apparatus 107, the input and output apparatus 108, and the clock 109.

Operation of Measurement Control Apparatus

Figure 4:
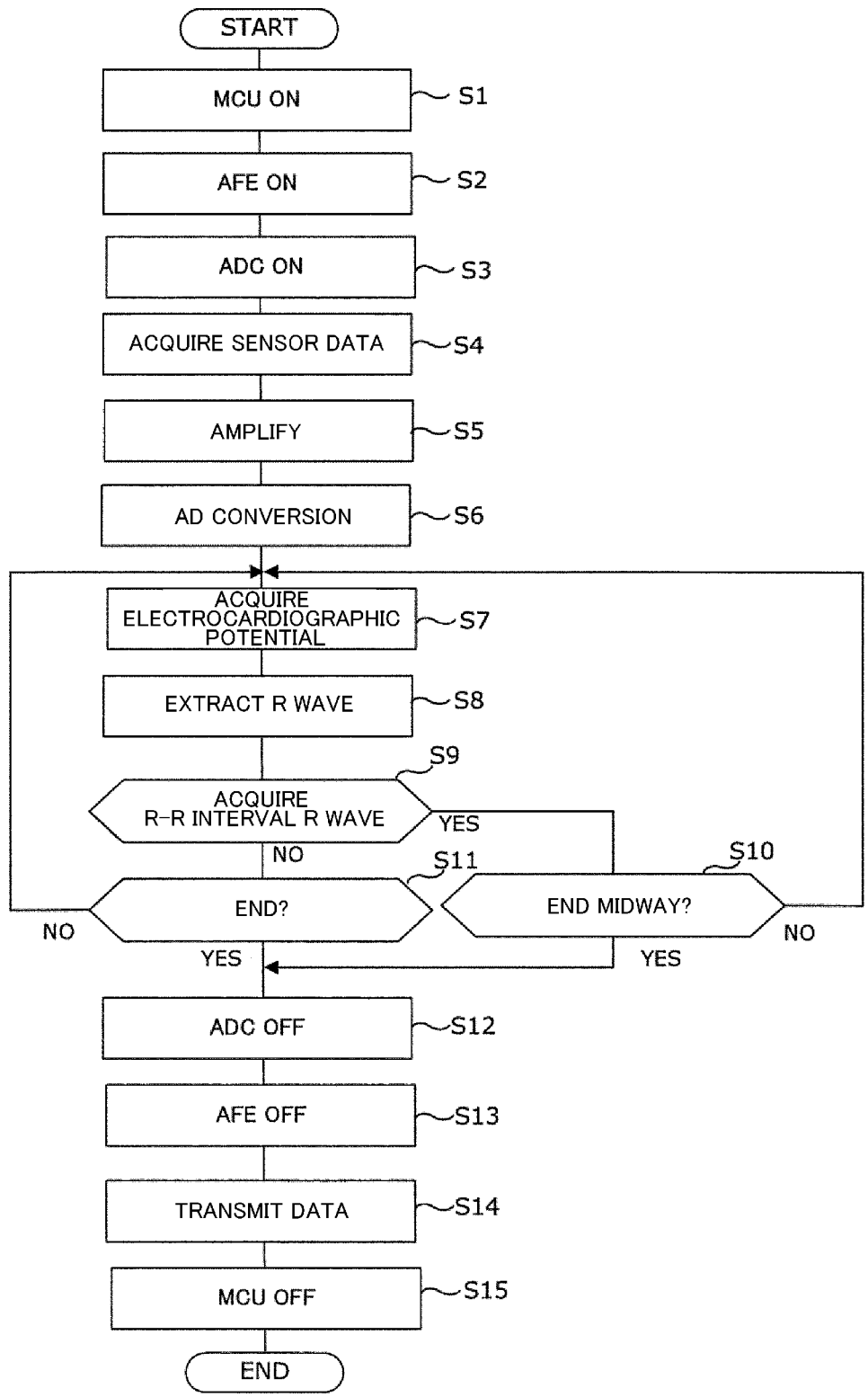
FIG. 4 is a flowchart illustrating an operation of the measurement control apparatus according to the embodiment of the present invention.

Next, an operation of the measurement control apparatus 1 having the above-described configuration will be described with reference to a flowchart of FIG. 4. The sensor 2 is attached to the user in advance, the electrocardiographic signal of the user is measured, and the following processing is executed. For example, the sensor 2 is configured of the electrocardiograph. Further, a period of time of the normal operation in which measurement of the heart rate is executed through the intermittent operation, that is, the set end time of the normal operation is stored in the storage unit 15 in advance. Further, information on a time in which the set standby operation is executed is stored in the storage unit 15.

First, the MCU 102 is activated (ON) (step S1). The AFE 105 is then activated (ON) (step S2). Thereafter, the analog signal acquired by the AFE 105 is stabilized and then power is supplied to the ADC 106 so that the ADC 106 is activated (ON) (step S3). Thereafter, the sensor data acquisition unit 10 acquires the electrocardiographic signal of the user from the sensor 2 (step S4). Then, the sensor data acquisition unit 10 amplifies the acquired electrocardiographic signal of the user (step S5). Specifically, the AFE 105 amplifies and outputs the signal.

Next, the sensor data acquisition unit 10 converts the amplified analog electrocardiographic signal into a digital signal at a set sampling frequency (step S6). Specifically, the ADC 106 converts the electrocardiographic signal as an analog signal into a digital signal and outputs the digital signal. Thereafter, output time-series data of an electrocardiographic potential of the user is stored in the storage unit 15 (step S7).

The extraction unit 11 then extracts the R wave from the time-series data of the electrocardiographic potential of the user stored in the storage unit 15 (step S8). The extraction unit 11 extracts the R wave appearing at regular intervals included in the time-series data of the electrocardiographic potential in step S8 and stores the R wave in the storage unit 15. More specifically, the extraction unit 11 can use a value considering a clearance before and after a peak derived from the R wave from a time difference value of the electrocardiographic potential as an index value for R wave extraction (see PTL 3). The extraction unit 11 can set a threshold value for time-series data of this index value according to an amplitude of the R wave, and can detect the R wave using the fact that a data value exceeds this threshold value (see PTL 4).

Thereafter, the interval acquisition unit 12 acquires the R-R interval indicating a period in which the R wave appears, from the plurality of R waves included in the electrocardiographic waveform of the user extracted in step S8 (step S9: YES). Specifically, when at least two R waves are extracted in step S8, the interval acquisition unit 12 can calculate the instantaneous heart rate from the period of the R waves appearing at time intervals adjacent to each other (see PTL 4).

The average heart rate can be calculated using a median, arithmetic mean, or moving average of the heart rate measured in the normal operation. Alternatively, an average value $HR_{ave}(i)$ may be calculated by Formula (1) below using an instantaneous heart rate $HR(i)$ obtained from data of an i-th R-R interval, an averaged value $HR_{ave}(i-1)$ of instantaneous heart rates up to an (i-1) th instantaneous heart rate, and a predetermined averaging coefficient r (for example, r=0, 1) as described in PTL 2.

$$HR_{ave}(i)=r \times HR(i)+(1-r) \times HR_{ave}(i-1) \quad (1)$$

The determination unit 13 then determines whether or not the R wave will have appeared by the set end time on the basis of the R-R interval acquired in step S9, and outputs a signal indicating that the measurement is to be terminated when the R wave will not have appeared (step S10: YES), and the process proceeds to step S12.

More specifically, the determination unit 13 uses Formula (2) below in determining whether or not to terminate the measurement.

Math. 1

$$t + \frac{60}{Y(X)}[\sec] > t_{measure} \quad (2)$$

In Formula (2) above, t indicates a measurement time in the normal operation, and X indicates the instantaneous heart rate or the average heart rate calculated from the latest R-R interval. Further, 60/Y(X) indicates a predicted time [sec] by which the next R wave appears, which is estimated from X.

When a left side of Formula (2) above exceeds the set end time $t_{measure}$, the determination unit 13 outputs the termination signal because no more R wave appears in the normal operation of the present intermittent operation.

The determination unit 13 can obtain Y(X) included in Formula (2) above by using any of Formulas (3) to (8) below.

For example, a case in which a plurality of R waves are missing due to, for example, a small amplitude of the R wave, and X has a value smaller than an actual value is considered. For example, Y(X) is calculated using Formula (3) below in consideration of the m missing R waves (m is an integer equal to or greater than 0).

$$Y(X)=(m+1)X \quad (3)$$

In addition to the consideration in Formula (3) above, it is considered that the heart rate varies sequentially. In this case, for example, Y(X) can be calculated using Formula (4) below in consideration of a heart rate variation amount ΔX. The heart rate variation amount ΔX is experimentally obtained in advance and stored in the storage unit 15.

$$Y(X)=(m+1)(X+\Delta X) \quad (4)$$

Alternatively, when m=0 in the example of Formula (3) above, that is, when missing of the R wave is not considered, Y(X) can be calculated using Formula (5) in additional consideration of an upper limit $X_{max}$ of the heart rate that may be generated.

Math. 2

$$Y(X) = \begin{cases} X & (X \leq X_{max}) \\ X_{max} & (X_{max} < X) \end{cases} \quad (5)$$

Further, as another example, in Formula (4) above in which the heart rate variation amount ΔX is considered, when m=0, that is, when the missing of the R wave is not considered, Y(X) can be calculated using Formula (6) below in additional consideration of the upper limit $X_{max}$ of the heart rate that may be generated.

Math. 3

$$Y(X) = \begin{cases} X+\Delta X & (X+\Delta X \leq X_{max}) \\ X_{max} & (X_{max} < X+\Delta X) \end{cases} \quad (6)$$

Alternatively, when missing of n or more (n is a natural number) R wave is considered, the determination unit 13 can calculate Y(X) using Formula (7) in additional consideration of the upper limit $X_{max}$ of the heart rate that may be generated in the example using Formula (3) above. r is a constant that takes 0≤r<1.

Math. 4

$$Y(X) = \begin{cases} (n+1)X & \left(X \leq \frac{X_{max}}{n+1}\right) \\ (n+r)X & \left(\frac{X_{max}}{n+1} < X \leq \frac{X_{max}}{n+r}\right) \\ (n-1+r)X & \left(\frac{X_{max}}{n+r} < X \leq \frac{X_{max}}{n-1+r}\right) \\ \vdots \\ (1+r)X & \left(\frac{X_{max}}{2+r} < X \leq \frac{X_{max}}{1+r}\right) \\ X_{max} & \left(\frac{X_{max}}{1+r} < X\right) \end{cases} \quad (7)$$

Alternatively, the determination unit 13 can calculate Y(X) using Formula (8) below in consideration of the heart rate variation amount ΔX used in Formula (4) in the example of Formula (7) above.

Math. 5

$$Y(X) = \begin{cases} (n+1)(X+\Delta X) & \left(X+\Delta X \leq \frac{X_{max}}{n+1}\right) \\ (n+r)(X+\Delta X) & \left(\frac{X_{max}}{n+1} < X+\Delta X \leq \frac{X_{max}}{n+r}\right) \\ (n-1+r)(X+\Delta X) & \left(\frac{X_{max}}{n+r} < X+\Delta X \leq \frac{X_{max}}{n-1+r}\right) \\ \vdots \\ (1+r)(X+\Delta X) & \left(\frac{X_{max}}{2+r} < X+\Delta X \leq \frac{X_{max}}{1+r}\right) \\ X_{max} & \left(\frac{X_{max}}{1+r} < X+\Delta X\right) \end{cases} \quad (8)$$

Referring back to FIG. 4, when the interval acquisition unit 12 has not acquired the R-R interval in step S9 (step S9: NO) and the set end time is reached (step S11: YES), the termination processing unit 14 proceeds to a process of terminating the measurement (step S12).

When the termination signal is output (step S10: YES) or the set end time is reached (step S11: YES), the termination processing unit 14 stops supply of power from the power supply apparatus 110 to the ADC 106 (step S12). Thereafter, the termination processing unit 14 stops supply of power from the power supply apparatus 11o to the AFE 105 (step S13).

Thereafter, the MCU 102 reads the heart rate of the user stored in the storage unit 15 to generate a packet, and transmits data from the transmission and reception unit 16 to an external terminal via the communication network NW (step S14). Thereafter, the termination processing unit 14 puts the MCU 102 in the standby state (OFF) (step S15). Through the above processing, the normal operation when the measurement control apparatus 1 performs the intermittent operation and measures the heart rate of the user ends, and the operation proceeds to the standby operation. The measurement control apparatus 1 can execute the normal operation again by repeating steps S1 to S15 again after a set standby period of time.

Figure 5:
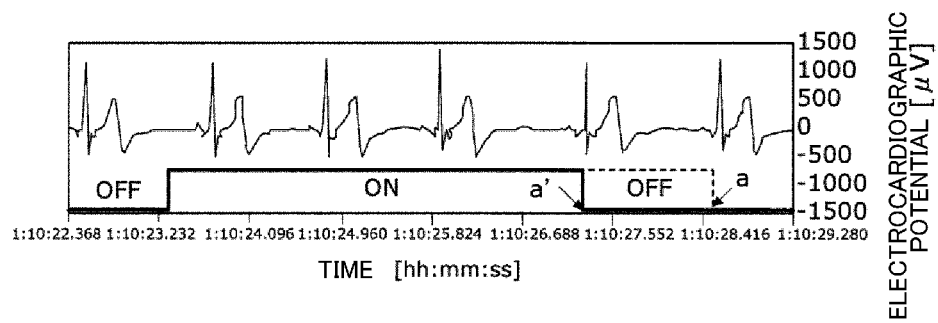
FIG. 5 is a diagram illustrating effects of the measurement control apparatus according to the embodiment of the present invention.

Next, an ON/OFF operation timing when the measurement control apparatus 1 according to the present embodiment performs an intermittent operation and determines a termination of the measurement of the electrocardiographic waveform of the user will be described with reference to FIG. 5. In FIG. 5, a horizontal axis represents time [hour: minute: second], and a vertical axis represents electrocardiographic potential [μV]. Further, as illustrated in FIG. 5, the operation timing (ON/OFF) of the measurement control apparatus 1 overlaps the electrocardiographic waveform.

Further, in FIG. 5, Formula (2) above is used when the determination unit 13 determines the termination. Further, Formula (3) above is used with m=0 in the calculation of Y(X) included in Formula (2). Further, in Formula (3), r=⅓, ΔX=15 [bpm], and $t_{measure}$=5 [sec]. Further, X is the median value of the instantaneous heart rate in the normal operation. When the determination unit 13 does not perform the determination as to the termination in the heart rate measurement, it can be seen that the measurement is continued at a set end time a even though no R wave appears (a broken line in FIG. 5).

However, in the present embodiment, when the determination unit 13 outputs the termination signal and the measurement is terminated, the measurement ends at a time a' before the set end time a. Therefore, it is possible to eliminate a useless measurement time in which no R wave is detected. Specifically, when the determination unit 13 determines the termination, an operation time is saved by about 26% as compared with the example of the related art (a broken line in FIG. 5), and power saving can be achieved.

As described above, according to the present embodiment, since the determination unit 13 determines whether or not the R wave will have appeared by the set end time on the basis of the R-R interval of the R wave of the user, it is possible to perform measurement of the biological information such as the heart rate of the user with more power saving.

In the described embodiment, a case in which the electrocardiographic waveform of the user is acquired by the sensor 2 including the electrocardiograph, the R-R interval is acquired from the electrocardiographic waveform, and the measurement of the heart rate and the determination as to the termination are performed has been described. However, the sensor 2 is not limited to the described specific example as long as information indicates, for example, a state of the user measured on the basis of the feature quantity of the biological information with periodicity, for example, when the number of beats of the user such as a pulse is measured by a pulse rate monitor.

Further, measurement targets that are controlled by the measurement control apparatus 1 are not limited to the measurement of the R-R interval of the electrocardiographic waveform and the heart rate, and other feature quantities included in the electrocardiographic waveform may be extracted. For example, the biological information of the user may be measured by observing P wave, Q wave, S wave, T wave, and the like.

Although the embodiments of the measurement control apparatus and the measurement control method of the present invention have been described above, the present invention is not limited to the described embodiments and it is possible to make various modifications that can be assumed by those skilled in the art within the scope of the invention defined in the claims.

REFERENCE SIGNS LIST

1 Measurement control apparatus
2 Sensor
10 Sensor data acquisition unit
11 Extraction unit
12 Interval acquisition unit
14 Termination processing unit
15 Storage unit
16 Transmission and reception unit
101 Bus
102 MCU
103 Main storage apparatus
104 Communication interface
105 AFE
106 ADC
107 Auxiliary storage apparatus
108 Input and output apparatus
109 Clock
110 Power supply apparatus
111 Display apparatus.

The invention claimed is:

1. A measurement control apparatus comprising:
a sensor data acquisition circuit configured to acquire biological information of a user measured by a sensor;
an extraction circuit configured to extract a feature quantity with periodicity from the biological information acquired by the sensor data acquisition circuit;
an interval acquisition circuit configured to acquire a period of the feature quantity;
a determination circuit configured to determine whether or not the feature quantity will have appeared by a set end time based on the period of the feature quantity; and
a termination processor configured to terminate an operation of the sensor data acquisition circuit in response to the determination circuit determining that the feature quantity will not have appeared by the set end time.

2. The measurement control apparatus according to claim 1, wherein the termination processor is configured to stop an acquisition of the biological information by the sensor data acquisition circuit.

3. The measurement control apparatus according to claim 1, wherein the termination processor is configured to stop a supply of power to the sensor data acquisition circuit.

4. The measurement control apparatus according to claim 1, wherein the sensor data acquisition circuit is configured to:
amplify an analog signal indicating the biological information to obtain an amplified analog signal; and
discretize the amplified analog signal in a preset sampling period to convert the analog signal into a digital signal.

5. The measurement control apparatus according to claim 1, wherein the sensor comprises an electrocardiograph, and wherein the sensor data acquisition circuit is configured to acquire an electrocardiographic signal of the user from the sensor.

6. The measurement control apparatus according to claim 5, wherein the extraction circuit is configured to extract an R wave included in the electrocardiographic signal as the feature quantity, wherein the interval acquisition circuit is configured to acquire an R-R interval indicating an interval of the R wave as the period, and wherein the determination circuit is configured to determine whether or not the R wave will have appeared at the set end time based on the R-R interval.

7. The measurement control apparatus according to claim 6, wherein the determination circuit is configured to determine whether or not the R wave will have appeared by the set end time through comparison with the set end time based on a time at which the sensor data acquisition circuit is configured to acquire the electrocardiographic signal and a predicted time by which a next R wave appears, and wherein the predicted time is estimated based on an instantaneous heart rate or an average heart rate calculated from a most recent R-R interval acquired by the interval acquisition circuit.

8. A measurement control method comprising:
a first step of acquiring biological information of a user measured by a sensor;
a second step of extracting a feature quantity with periodicity from the biological information acquired in the first step;
a third step of acquiring a period of the feature quantity;
a fourth step of determining whether or not the feature quantity will have appeared by a set end time based on the period of the feature quantity; and
a fifth step of terminating an acquisition of the biological information in response to determining that the feature quantity will not have appeared by the set end time.

9. The method according to claim 8, wherein the first step comprises acquiring the biological information with a sensor data acquisition circuit, and wherein the fifth step comprises stopping a supply of power to the sensor data acquisition circuit in response to determining that the feature quantity will not have appeared by the set end time.

10. The method according to claim 9, wherein the sensor data acquisition circuit is configured to:
   amplify an analog signal indicating the biological information to obtain an amplified analog signal; and
   discretize the amplified analog signal in a preset sampling period to convert the analog signal into a digital signal.

11. The method according to claim 8, wherein the first step comprises acquiring the biological information as an electrocardiographic signal of the user.

12. The method according to claim 11, wherein:
   the second step comprises extracting an R wave included in the electrocardiographic signal as the feature quantity;
   the third step comprises acquiring an R-R interval indicating an interval of the R wave as the period; and
   the fourth step comprises determining whether or not the R wave will have appeared at the set end time based on the R-R interval.

13. The method according to claim 12, wherein the fourth step comprises determining whether or not the R wave will have appeared by the set end time through comparison with the set end time based on a time at which an electrocardiographic signal is acquired and a predicted time by which a next R wave appears, and wherein the predicted time is estimated based on an instantaneous heart rate or an average heart rate calculated from a most recently acquired R-R interval.

* * * * *